United States Patent
Lee (10) Patent No.: US 10,745,451 B2
(45) Date of Patent: Aug. 18, 2020

(54) SCORPION TOXIN FUSION PROTEIN WITH ENHANCED SKIN CELL PROLIFERATION EFFECT AND COSMETIC COMPOSITION FOR ANTI-WRINKLE, ENHANCING SKIN ELASTICITY AND ANTI-AGING COMPRISING THE SAME AS AN EFFECTIVE INGREDIENT

(71) Applicants: NEXGEN BIOTECHNOLOGIES, INC., Seoul (KR); Sun Kyo Lee, Gyeonggi-do (KR)

(72) Inventor: Sun Kyo Lee, Gyeonggi-do (KR)

(73) Assignees: NEXGEN BIOTECHNOLOGIES, INC., Seoul (KR); Sun Kyo Lee, Gyeonggi-Do (KR)

( * ) Notice: Subject to any disclaimer, the term of this patent is extended or adjusted under 35 U.S.C. 154(b) by 54 days.

(21) Appl. No.: 16/328,107

(22) PCT Filed: Aug. 25, 2017

(86) PCT No.: PCT/KR2017/009301
§ 371 (c)(1),
(2) Date: Feb. 25, 2019

(87) PCT Pub. No.: WO2018/038567
PCT Pub. Date: Mar. 1, 2018

(65) Prior Publication Data
US 2019/0185527 A1    Jun. 20, 2019

(30) Foreign Application Priority Data
Aug. 25, 2016 (KR) .......... 10-2016-0108338

(51) Int. Cl.
| A61K 38/02 | (2006.01) |
| C07K 14/435 | (2006.01) |
| A61K 8/64 | (2006.01) |
| A61Q 19/08 | (2006.01) |
| C12N 15/62 | (2006.01) |
| C12N 15/70 | (2006.01) |
| A61Q 19/00 | (2006.01) |
| C12P 21/00 | (2006.01) |
| C07K 14/47 | (2006.01) |
| A61K 8/97 | (2017.01) |
| C12P 21/02 | (2006.01) |

(52) U.S. Cl.
CPC .......... *C07K 14/43522* (2013.01); *A61K 8/64* (2013.01); *A61K 8/97* (2013.01); *A61Q 19/00* (2013.01); *A61Q 19/08* (2013.01); *C07K 14/435* (2013.01); *C07K 14/47* (2013.01); *C12N 15/62* (2013.01); *C12N 15/70* (2013.01); *C12P 21/00* (2013.01); *C12P 21/02* (2013.01)

(58) Field of Classification Search
None
See application file for complete search history.

(56) References Cited

U.S. PATENT DOCUMENTS

2011/0027221 A1   2/2011   Fu et al.
2014/0335155 A1   11/2014  Yang et al.

FOREIGN PATENT DOCUMENTS

| KR | 10-2005-0036946 A | 4/2005 |
| KR | 20150056022 A | 5/2015 |
| KR | 10-1636851 B1 | 7/2016 |
| KR | 10-1678393 B1 | 12/2016 |
| WO | WO 03/101475 A1 | 12/2003 |
| WO | WO 2004/005520 A1 | 1/2004 |
| WO | WO 2007/086879 A2 | 8/2007 |
| WO | WO 2011097533 A1 | 8/2011 |

OTHER PUBLICATIONS

Supplementary European Search Report for EP17843987 dated Mar. 20, 2020 from European patent office in a counterpart European patent application.
Database UniProt [online], Nov. 1, 1995 "RecName: Full= Chlorotoxin {ECO:0000303:PubMed:12454020, ECO:0000303:PubMed:8383429}; Short=CTX;Short=C1Tx {ECO:0000303:PubMed:12454020},AltName: INN=Tozuleristide;", XP002798008, retrieved from EBI accession No. UNIPROT: P45639 Database accession No. PJ45639 *sequence*.
International Search Report for PCT/KR2017/009301 dated Dec. 12, 2017.
Xu, Tengfei et al., "Identification of two novel Chlorotoxin derivatives CA4 and CTX-23 with chemotherapeutic and anti-angiogenic potential", Scientific Reports, vol. 6, mp.19799, Feb. 2016.
Kim, Hyun-young, "Cancer cell metaplasia is a scorpion poison", New York JoongAng Ilbo, Jul. 2009 (English translation is also submitted herewith.).
Hanahan, D., "Studies on Transformation of *Escherichia coli* with Plasmids", Mol. Biol., 166:557-580, Jan. 1983.

*Primary Examiner* — Thomas S Heard
(74) *Attorney, Agent, or Firm* — The PL Law Group, PLLC (57) ABSTRACT

A fusion protein having the amino acid sequence of SEQ ID NO: 3 or SEQ ID NO: 4 has enhanced skin cell proliferation effect. A composition includes, as an effective ingredient, the fusion protein for improving skin wrinkle, skin elasticity, and anti-aging. Because the composition has an excellent cell proliferation effect and an effect of improving skin wrinkle and enhancing skin elasticity, it is expected to be used advantageously in the field of functional cosmetics.

19 Claims, 6 Drawing Sheets
Specification includes a Sequence Listing.

Fig. 2
Diagram showing EGF-CLT expression

SCORPION TOXIN FUSION PROTEIN WITH ENHANCED SKIN CELL PROLIFERATION EFFECT AND COSMETIC COMPOSITION FOR ANTI-WRINKLE, ENHANCING SKIN ELASTICITY AND ANTI-AGING COMPRISING THE SAME AS AN EFFECTIVE INGREDIENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/009301, filed Aug. 25, 2017, which claims priority to the benefit of Korean Patent Application No. 10-2016-0108338 filed in the Korean Intellectual Property Office on Aug. 25, 2016, the entire contents of which are incorporated herein by reference.

TECHNICAL FIELD

The present invention relates to a scorpion toxin fusion protein with enhanced skin cell proliferation effect and a cosmetic composition comprising, as an effective ingredient, the scorpion toxin fusion protein for improving skin wrinkle, skin elasticity, and anti-aging.

BACKGROUND ART

Thioredoxin (TRX) is present in every living organism, and it is a small protein of 12 kDa which has 2 oxidation-reduction activities at an active site (Cys-Gly-Pro-Cys). TRX containing cysteine (Cys) thiol group is involved with various anti-oxidation reactions including suppression of cell apoptosis which depends on oxidation-reduction reaction and stabilization of transcription factors related to oxidative stress.

It is known that oxidative stress is one of the determinants of life span of a cell and an organism. To prove the relationship between the protective role by oxidation-reduction reaction of TRX and extension of life span, expression of TRX is suppressed via shRNA in normal human skin fibroblast. As a result, it was shown that loss of TRX can rapidly induce skin aging in human skin fibroblast based on activation of a pathway for suppressing p16INK4a and p53/p21Cip1/Waf1 tumors. Other than the activity of protecting cells against oxidative stress, TRX suppresses cell aging.

Upon binding to a receptor for an epidermal growth factor present on a surface of a cell, the human epidermal growth factor (hEGF) induces a dimerization of a receptor for an epidermal growth factor. A dimeric receptor for an epidermal growth factor activates the tyrosine kinase present in the receptor to induce an intracellular signal transduction system. As a result of a series of such processes, glycolysis, protein synthesis, or the like are promoted in a cell, eventually leading to cell growth.

The human epidermal growth factor playing a critical role in skin regeneration decreases according to a progress of aging. As a result, a reduction in skin cell proliferation and transfer is caused, and thus it can be a cause of skin aging, increased wrinkles, and reduced skin elasticity. At present moment, it is used as a pharmaceutical product or a functional cosmetic product for promoting skin cell growth.

Use of an excessive amount of toxin may cause a damage on human body, but use of toxin in suitable amount may be useful for human body. Continuous studies on toxins have been limited to a medicinal field. However, at present moment, various studies are being carried out by cosmetics industry, in particular, in the field of skin care. In this regard, botulinum toxin and spider toxin proteins are used as a new material for improving skin wrinkle and maintaining skin elasticity. Spider toxin protein is also confirmed to have an excellent skin cell proliferation effect.

Under the circumstances, to maximize the skin cell proliferation effect of scorpion toxin protein by combining the anti-aging activity based on anti-aging effect of human thioredoxin and skin regenerating activity of human epidermal growth factor with the scorpion toxin protein, the inventors of the present invention carried out a study on development of new proteins. As a result, the inventors successfully developed a novel fusion protein including the human thioredoxin and scorpion toxin and a novel fusion protein including the human epidermal growth factor and scorpion toxin by bridging the anti-oxidation based anti-aging effect of human thioredoxin and skin regenerating activity of human epidermal growth factor to the skin cell proliferation effect of scorpion toxin protein. Furthermore, as a result of confirming the safety for skin application, anti-aging effect, activity of skin regeneration (wrinkle improvement) and skin elasticity enhancement by using the aforementioned fusion protein in a cosmetic composition, the inventors finally completed the present invention.

Meanwhile, in Korean Patent Application Publication No. 2012-0114397, "Chlorotoxin polypeptides and conjugates and use thereof" is disclosed, and in Korean Patent Application Publication No. 2015-0056022, "Cosmetic composition for skin improvement comprising fusion protein of epidermal growth factor" is disclosed. However, a scorpion toxin fusion protein with enhanced skin cell proliferation effect and a cosmetic composition for improving skin wrinkle, skin elasticity, and anti-aging comprising the fusion protein as an effective ingredient of the present invention have not been described yet.

SUMMARY

The present invention is devised in view of the demand described above, and the inventors of the present invention developed a novel fusion protein including the human thioredoxin and scorpion toxin and a novel fusion protein including the human epidermal growth factor and scorpion toxin wherein the novel fusion proteins have an effect of improving skin wrinkle, skin elasticity, and anti-aging. Furthermore, by confirming that those fusion proteins are effective for improving skin wrinkle, skin elasticity, and anti-aging, they completed the present invention accordingly.

To solve the problems described above, the present invention provides a human thioredoxin-scorpion toxin fusion protein having an enhanced skin cell proliferation and anti-oxidation effect which consists of the amino acid sequence of SEQ ID NO: 3.

The present invention further provides a human epidermal growth factor-scorpion toxin fusion protein having an enhanced skin cell proliferation effect which consists of the amino acid sequence of SEQ ID NO: 4.

The present invention further provides a gene encoding the human thioredoxin-scorpion toxin fusion protein or human epidermal growth factor-scorpion toxin fusion protein.

The present invention further provides a recombinant vector comprising the aforementioned gene, and a host cell transformed with the recombinant vector.

The present invention further provides a method for producing a human thioredoxin-scorpion toxin fusion protein or a human epidermal growth factor-scorpion toxin fusion protein in a host cell comprising transforming a host cell with the aforementioned recombinant vector to overexpress a gene encoding a human thioredoxin-scorpion toxin fusion protein or a human epidermal growth factor-scorpion toxin fusion protein.

The present invention further provides a human thioredoxin-scorpion toxin fusion protein or a human epidermal growth factor-scorpion toxin fusion protein produced by the aforementioned method.

The present invention further provides a cosmetic composition for improving skin wrinkle, enhancing skin elasticity, and anti-aging comprising, as an effective ingredient, the human thioredoxin-scorpion toxin fusion protein having an enhanced skin cell proliferation effect and anti-oxidation activity which consists of the amino acid sequence of SEQ ID NO: 3.

The present invention still further provides a cosmetic composition for improving skin wrinkle and enhancing skin elasticity comprising, as an effective ingredient, the human epidermal growth factor-scorpion toxin fusion protein having an enhanced skin cell proliferation effect which consists of the amino acid sequence of SEQ ID NO: 4.

The fusion protein including the human thioredoxin and scorpion toxin and the fusion protein including the human epidermal growth factor and scorpion toxin of the present invention are expressed in the form of inclusion body in *Escherichia coli*, and thus the instability issue of the fusion protein is resolved and simplification of production step is achieved. Furthermore, as the above proteins have an excellent effect of improving skin wrinkle, enhancing skin elasticity, and anti-aging based on their skin regeneration effect, they are expected to be used widely as an effective ingredient of a functional cosmetic composition.

DETAILED DESCRIPTION

To achieve the purpose of the present invention, the present invention provides a human thioredoxin-scorpion toxin fusion protein having an enhanced skin cell proliferation and anti-oxidation effect which consists of the amino acid sequence of SEQ ID NO: 3.

The scope of the human thioredoxin-scorpion toxin fusion protein according to the present invention includes a protein having an amino acid sequence represented by SEQ ID NO: 3, and also functional equivalents of the protein. The term "functional equivalent" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 3, and it indicates a protein exhibiting substantially the same physiological activity as the protein represented by SEQ ID NO: 3. The expression "substantially the same physiological activity" means a skin cell proliferation activity and an anti-oxidation activity. Furthermore, included in the human thioredoxin-scorpion toxin fusion protein are a fragment, a derivative, and an analogue thereof. The terms "fragment", "derivative", and "analogue" that are used herein indicate a polypeptide which has substantially the same physiological function or activity as the human thioredoxin-scorpion toxin fusion protein of the present invention.

The human thioredoxin-scorpion toxin fusion protein of the present invention preferably consists of the amino acid sequence of SEQ ID NO: 3, and it may be a novel protein which is produced by fusion between the human thioredoxin protein consisting of the 1$^{st}$ to the 105$^{th}$ amino acids and the scorpion toxin protein consisting of the 106$^{th}$ to the 140$^{th}$ amino acids of the above amino acid sequence.

The present invention further provides a human epidermal growth factor-scorpion toxin fusion protein having an enhanced skin cell proliferation effect which consists of the amino acid sequence of SEQ ID NO: 4.

The scope of the human epidermal growth factor-scorpion toxin fusion protein according to the present invention includes a protein having an amino acid sequence represented by SEQ ID NO: 4, and also functional equivalents of the protein. Specific descriptions relating to the functional equivalents of the protein are the same as those described above.

The human epidermal growth factor-scorpion toxin fusion protein of the present invention preferably consists of the amino acid sequence of SEQ ID NO: 4, and it may be a novel protein which is produced by fusion between the human epidermal growth factor protein consisting of the $1^{st}$ to the $54^{th}$ amino acids and the scorpion toxin protein consisting of the $55^{th}$ to the $89^{th}$ amino acids of the above amino acid sequence.

The present invention further provides a gene encoding the human thioredoxin-scorpion toxin fusion protein or human epidermal growth factor-scorpion toxin fusion protein.

This gene encoding the human thioredoxin-scorpion toxin fusion protein may consist of a nucleotide sequence of *E. coli* codon-optimized SEQ ID NO: 1, but not limited thereto. Preferably, the gene encoding the human thioredoxin-scorpion toxin fusion protein according to the present invention may include a nucleotide sequence of SEQ ID NO: 1. Furthermore, homologues of the nucleotide sequence are also within the scope of the present invention. Specifically, the above described gene may comprise a nucleotide sequence which has preferably at least 70%, more preferably at least 80%, still more preferably at least 90%, and most preferably at least 95% homology with the nucleotide sequence of SEQ ID NO: 1. The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

"Codon optimization" means a modification of codon of a polynucleotide encoding a protein with a codon that is used first than others in a specific organism such that the coded protein can be more efficiently expressed therein. Because most amino acids are described by several codons that are referred to as "synonym" or "synonymous codon", genetic codes have degeneracy. However, codon usage by a specific organism is not random, and it is rather biased to specific codon triplets. Such codon usage bias may be even higher in relation with a certain gene, a gene with common function or ancestor origin, protein expressed at high level vs. proteins with low copy number, or a group protein coding region of a genome of an organism. The nucleotide sequence of SEQ ID NO: 1 of the present invention is a sequence which has been optimized to *E. coli* codon such that the gene encoding human thioredoxin-scorpion toxin fusion protein can be expressed well in *E. coli*.

Furthermore, the gene encoding the human epidermal growth factor-scorpion toxin fusion protein may consist of a nucleotide sequence of *E. coli* codon-optimized SEQ ID NO: 2, but not limited thereto. Preferably, the gene may include a nucleotide sequence of SEQ ID NO: 2. Furthermore, homologues of the nucleotide sequence are also within the scope of the present invention, and specific descriptions relating to the homologues are as described in the above.

The present invention further provides a recombinant vector comprising the aforementioned gene and a host cell transformed with the recombinant vector.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

According to the present invention, the gene encoding human thioredoxin-scorpion toxin fusion protein or human epidermal growth factor-scorpion toxin fusion protein can be inserted to a recombinant expression vector. The term "recombinant expression vector" means bacteria plasmid, phage, yeast plasmid, plant cell virus, mammalian cell virus, or other vector. Any plasmid and vector can be generally used if it can replicate and is stabilized in a host. Important characteristics of the expression vector include that it comprises a replication origin, a promoter, a marker gene, and a translation control element.

The expression vector comprising the gene sequence encoding the human thioredoxin-scorpion toxin fusion protein or human epidermal growth factor-scorpion toxin fusion protein and an appropriate signal for regulating transcription/translation can be constructed according to a method which is well known to a skilled person in the art. The method includes an in vitro recombinant DNA technique, a DNA synthesis technique, and an in vivo recombinant technique. For inducing mRNA synthesis, the DNA sequence can be effectively linked to a suitable promoter present in the expression vector. In addition, the expression vector may comprise a ribosome binding site as a translation initiation site and a transcription terminator.

The recombinant vector according to one embodiment of the present invention is prepared by in-frame fusion of 5' terminal (NdeI restriction enzyme site) and 3' terminal (XhoI restriction enzyme site) of the synthesized gene encoding the human thioredoxin-scorpion toxin fusion protein or human epidermal growth factor-scorpion toxin fusion protein to pET22b vector, and it is a vector characterized in that it can produce the human thioredoxin-scorpion toxin fusion protein or human epidermal growth factor-scorpion toxin fusion protein based on effective expression of the aforementioned gene with an aid of lac promoter (lac promoter) and lad repressor (lad repressor).

For a host cell having an ability of having stable and continuous cloning and expression of the vector of the present invention in a prokaryotic cell, any host cell known in the pertinent art can be used. Examples of the prokaryotic cells include, *Bacillus* sp. strain including *E. coli* Rosetta, *E. coli* JM109, *E. coli* BL21, *E. coli* RR1, *E. coli* LE392, *E. coli* B, *E. coli* X 1776, *E. coli* W3110, *Bacillus subtillus, Bacillus thuringiensis* and the like, and intestinal bacteria and strains including *Salmonella typhimurium, Serratia marcescens* and various *Pseudomonas* sp. etc.

Furthermore, when an eukaryotic cell is transformed with the vector of the present invention, yeast (*Saccharomyce cerevisiae*), an insect cell, a human cell (for example, CHO (Chinese hamster ovary) cell line, W138, BHK, COS-7, 293, HepG2, 3T3, RIN, and MDCK cell line), a plant cell, and the like can be used as a host cell.

The host cell transformed with the recombinant vector according to one embodiment of the present invention can be *E. coli* Rosetta2 (DE3) pLysS, but not limited thereto.

When a host cell is a prokaryotic cell, delivery of the recombinant vector of the present invention into a host cell can be carried out by $CaCl_2$ method, Hanahan's method (Hanahan, D., J. Mol. Biol., 166:557-580 (1983)) or an electroporation method, and the like. In addition, when a host cell is an eukaryotic cell, the vector can be introduced to a host cell by a microinjection method, calcium phosphate precipitation method, an electroporation method, a liposome-mediated transfection method, DEAE-dextran treatment method, or a gene bombardment method, and the like.

The present invention further provides a method for producing a human thioredoxin-scorpion toxin fusion protein or a human epidermal growth factor-scorpion toxin fusion protein in a host cell comprising transforming a host cell with the aforementioned recombinant vector to overexpress a gene encoding a human thioredoxin-scorpion toxin fusion protein or a human epidermal growth factor-scorpion toxin fusion protein.

One embodiment of the present invention includes large-scale production of the fusion protein including the human thioredoxin and scorpion toxin and fusion protein including the human epidermal growth factor and scorpion toxin, in which a fusion gene encoding 140 amino acids of the human thioredoxin and scorpion toxin and a fusion gene encoding 89 amino acids of the human epidermal growth factor and scorpion are synthesized, a recombinant vector containing the fusion gene is prepared, and a host microorganism is transformed with the recombinant vector to produce the fusion proteins in large amount.

Meanwhile, by adopting an intracellular production mode which is more effective than extracellular secretion, the inventors of the present invention produce a large amount of the fusion protein including the human thioredoxin and scorpion toxin and fusion protein including the human epidermal growth factor and scorpion toxin.

With regard to the method according to one embodiment of the present invention, the host cell can be preferably *E. coli*, and more preferably *E. coli* Rosetta2 (DE3) pLysS, but not limited thereto.

As for the method for culturing the recombinant microorganism of the present invention, i.e., transformant, a method commonly used for culturing a host can be employed. Furthermore, the culture method which can be used may be any common method used for culture of microorganisms including batch type culture, fluid batch type culture, continuous culture, and reactor type culture. As for the medium for culturing a transformant which is obtained by using bacteria like *E. coli* as a host, a complete medium or a synthetic medium, for example, LB (10% Tryptone, 10% Sodium chloride, 5% Yeast extract) medium, BSB (1% Tryptone, 0.5% Yeast extract, 0.1% HEPES, 1% glucose, pH 7.0), an a medium by Nexgen Biotechnologies Inc. can be exemplified. Furthermore, temperature for culture can be within a suitable temperature range, and according to culture at about 37° C., the human thioredoxin-scorpion toxin fusion protein or the human epidermal growth factor-scorpion toxin fusion protein can be accumulated in cell bodies and then collected therefrom. It is also possible to add to a culture liquid an antibiotic like kanamycin, ampicillin, tetracycline, chloramphenicol, and streptomycin. When transformed microorganisms are cultured by using an expression vector with inducible promoter, an inducing material that is suitable for the type of the promoter can be added to a medium. Examples of the inducing material include isopropyl-D-thiogalactopyranoside (IPTG) and lactose.

Obtainment of human thioredoxin-scorpion toxin fusion protein or human epidermal growth factor-scorpion toxin fusion protein can be achieved by collecting by centrifuge the cell bodies or supernatant from a culture to be obtained, carrying out isolation by using cell disruption, extraction, or ultrafiltration method, and purification based on affinity chromatography, cation or anion exchange chromatography, or gel filtration, or a suitable combination thereof. Confirmation of a purified product to be obtained as a target protein can be carried out by according to a common method, for example, by SDS-polyacrylamide gel electrophoresis, Western blotting, or by using a kit for confirming human epidermal growth factor or the like.

By measuring the cell proliferation effect and anti-oxidation effect on HDFa cell exhibited by the human thioredoxin-scorpion toxin fusion protein or human epidermal growth factor-scorpion toxin fusion protein, the activity of the human thioredoxin-scorpion toxin fusion protein or human epidermal growth factor-scorpion toxin fusion protein can be determined.

Furthermore, to see any promoted synthesis of collagen fiber that is one of the ways for suppressing skin aging caused by ultraviolet ray stimulation, fibroblast was treated with the proteins of the present invention and an evaluation was made in terms of promoted collagen synthesis.

The present invention further provides a human thioredoxin-scorpion toxin fusion protein or a human epidermal growth factor-scorpion toxin fusion protein produced by the aforementioned method.

The present invention further relates to a cosmetic composition comprising, as an effective ingredient, the human thioredoxin-scorpion toxin fusion protein or human epidermal growth factor-scorpion toxin fusion protein.

The present invention further provides a cosmetic composition for improving skin wrinkle, enhancing skin elasticity, and anti-aging comprising, as an effective ingredient, the human thioredoxin-scorpion toxin fusion protein having an enhanced skin cell proliferation effect and anti-oxidation activity which consists of the amino acid sequence of SEQ ID NO: 3.

The present invention still further provides a cosmetic composition for improving skin wrinkle and enhancing skin elasticity comprising, as an effective ingredient, the human epidermal growth factor-scorpion toxin fusion protein having an enhanced skin cell proliferation effect which consists of the amino acid sequence of SEQ ID NO: 4.

In the cosmetic composition according to one embodiment of the present invention, content of the human thioredoxin-scorpion toxin fusion protein or human epidermal growth factor-scorpion toxin fusion protein may be 0.000001 to 0.001% by weight relative to the total weight of the cosmetic composition, but not limited thereto. If the protein content is lower than 0.000001% by weight, the effect is not obtained as the protein activity is not exhibited in skin. On the other hand, if the protein content is higher than 0.001% by weight, the enhanced effect may be insignificant compared to the increase in content and also there may be a problem in terms of the safety and stability of the formulation.

In the cosmetic composition of the present invention, components that are typically used for a cosmetic composition are included in addition to the effective ingredients that are described above. Examples thereof include a lipid material, an organic solvent, a dissolution agent, a condensation agent, a gelling agent, a softening agent, an anti-oxidant, a suspension agent, a stabilizer, a foaming agent, an aroma, a surface active agent, water, an ionic or non-ionic emulsifier, a filler, a metal ion sequestering agent, a chelating agent, a preservative, vitamin, a blocking agent, a moisturizing agent, essential oil, a dye, a pigment, a hydrophilic or liphophilic activating agent, a common auxiliary agent such as lipid vesicle, and a carrier.

The composition of the present invention can be prepared in any formulation which is generally prepared in the pertinent art. For example, the composition may be formulated into a solution, a suspension, an emulsion, a paste, a gel, a crème, a lotion, a powder, an oil, a powder foundation, an emulsion foundation, a wax foundation, a spray, or the like, but not limited thereto. More specifically, the composition may be formulated into a skin, a skin softener, a skin toner, an astringent, a lotion, a milk lotion, a moisture lotion, a nutrition lotion, a massage crème, a nutrition crème, an eye crème, a moisture crème, a hand crème, an essence, a nutrition essence, a pack, a cleansing foam, a cleansing water, a cleansing lotion, a cleansing crème, a body lotion, a body cleanser, a soap, a powder, or the like.

In a case in which the cosmetic composition of the present invention has a formulation type of paste, crème, or gel, it is possible to use, as a carrier component, animal oil, plant oil, wax, paraffin, starch, tragacanth, cellulose derivatives, polyethylene glycol, silicone, bentonite, silica, talc, or zinc oxide.

In a case in which the cosmetic composition of the present invention has a formulation type of solution or emulsion, a solvent, a dissolution agent, or an emulsifier is used as a carrier component, and examples thereof include water, ethanol, isopropyl alcohol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

In a case in which the cosmetic composition of the present invention has a formulation type of suspension, it is possible to use, as a carrier component, a liquid phase diluent such as water, ethanol, or propylene glycol, a suspension agent such as ethoxylated isostearyl alcohol, polyoxyethlyene sorbitol ester, or polyoxyethylene sorbitan ester, microcrystalline cellulose, aluminum metahydroxide, bentonite, agar, or tragacanth.

In a case in which the cosmetic composition of the present invention has a formulation type of surfactant-free cleanser, it can be wiped, detached, or washed with water after application on skin. Specific examples of the formulation type of surfactant-free cleanser include cleansing crème, cleansing lotion, cleansing water, and cleansing gel, but it is not limited thereto.

In a case in which the cosmetic composition of the present invention has a formulation type of powder, it is possible to use, as a carrier component, lactose, talc, silica, aluminum hydroxide, calcium silicate, or polyamide powder.

The cosmetic composition comprising the fusion protein which includes the human thioredoxin and scorpion toxin or the fusion protein which includes the human epidermal growth factor and scorpion toxin according to the present invention was tested first in terms of skin safety, and then the effect of the fusion protein which includes the human thioredoxin and scorpion toxin and the effect of the fusion protein which includes the human epidermal growth factor and scorpion toxin like anti-aging effect of the fusion protein which includes the human thioredoxin and scorpion toxin or the fusion protein which includes the human epidermal growth factor and scorpion toxin were determined.

Hereinbelow, the present invention is explained in greater detail in view of the Examples. However, it is evident that the following Examples are given only for exemplification of the present invention and by no means the present invention is limited to the following Examples.

EXAMPLES

Example 1. Preparation of Recombinant Vector and Transformed Recombinant Microorganism for Producing Fusion Protein Including Human Thioredoxin and Scorpion Toxin and Fusion Protein including Human Epidermal Growth Factor and Scorpion Toxin The optimized gene encoding the fusion protein including the human thioredoxin and scorpion toxin or the fusion protein including the human epidermal growth factor and scorpion toxin, recombinant vector, and transformed recombinant microorganism were prepared according to the following method. By using as a template the gene encoding the fusion protein including the human thioredoxin and scorpion toxin or the fusion protein including the human epidermal growth factor and scorpion toxin, the gene (SEQ ID NO: 1) encoding the fusion protein including the human thioredoxin and scorpion toxin (SEQ ID NO: 3) in which 140 amino acids are encoded and the gene (SEQ ID NO: 2) encoding the fusion protein including the human epidermal growth factor and scorpion toxin (SEQ ID NO: 4) in which 89 amino acids are encoded were synthetically prepared. The primers used therefor are as described below.

The primers for synthesis of a fusion protein including the human thioredoxin and scorpion toxin are as follows.

```
Forward primer:
                                      (SEQ ID NO: 5)
5'-AAGGAGATATACATATGGTGAAGCAGATCGAG-3'

Reverse primer:
                                      (SEQ ID NO: 6)
5'-CGTCACGGACACGGCAGACTAATTCATTAATGGTG-3'

Sense primer:
                                      (SEQ ID NO: 7)
5'-CACCATTAATGAATTAGTCATGTGCATGCCGTGCTTC-3'

Antisense primer:
                                      (SEQ ID NO: 8)
5'-GAAGCACGGCATGCACATGACTAATTCATTAATGGTG-3'
```

The primers for synthesis of a fusion protein including the human epidermal growth factor and scorpion toxin are as follows.

```
Forward primer:
                                      (SEQ ID NO: 9)
5'-AAGGAGATATACATATGAACTCAGACTCTGAGTGC-3'

Reverse primer:
                                      (SEQ ID NO: 10)
5'-GGTGGTGGTGCTCGAGACGGCACAGGCACTGCGG-3'

Sense primer:
                                      (SEQ ID NO: 11)
5'-AAATGGTGGGAGTTGCGCATGTGCATGCCGTGCTTC-3'

Antisense primer:
                                      (SEQ ID NO: 12)
5'-GAAGCACGGCATGCACATGCGCAACTCCCACCATTT-3'
```

Figure 1:
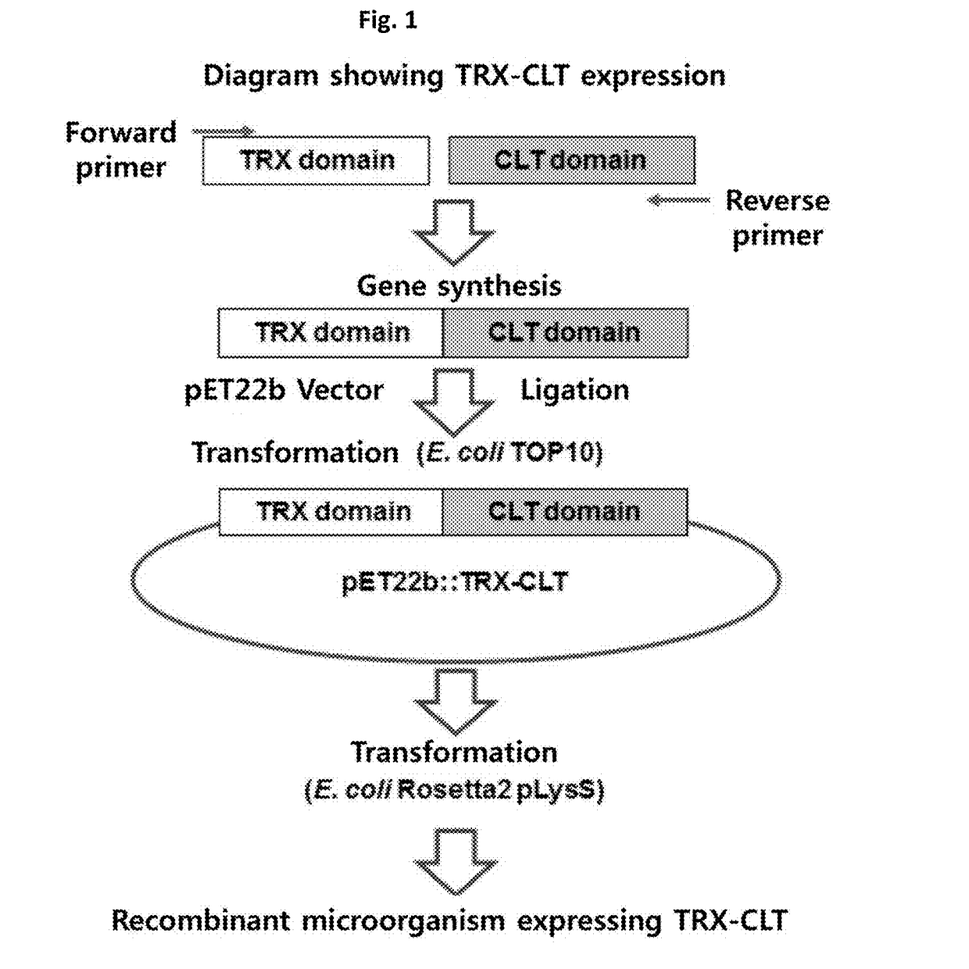
FIG. 1 is a schematic drawing illustrating the preparation of a recombinant plasmid (pET22b::TRX-CLT) of a fusion gene including human thioredoxin and scorpion toxin, and transformation with the recombinant plasmid.
Figure 2:
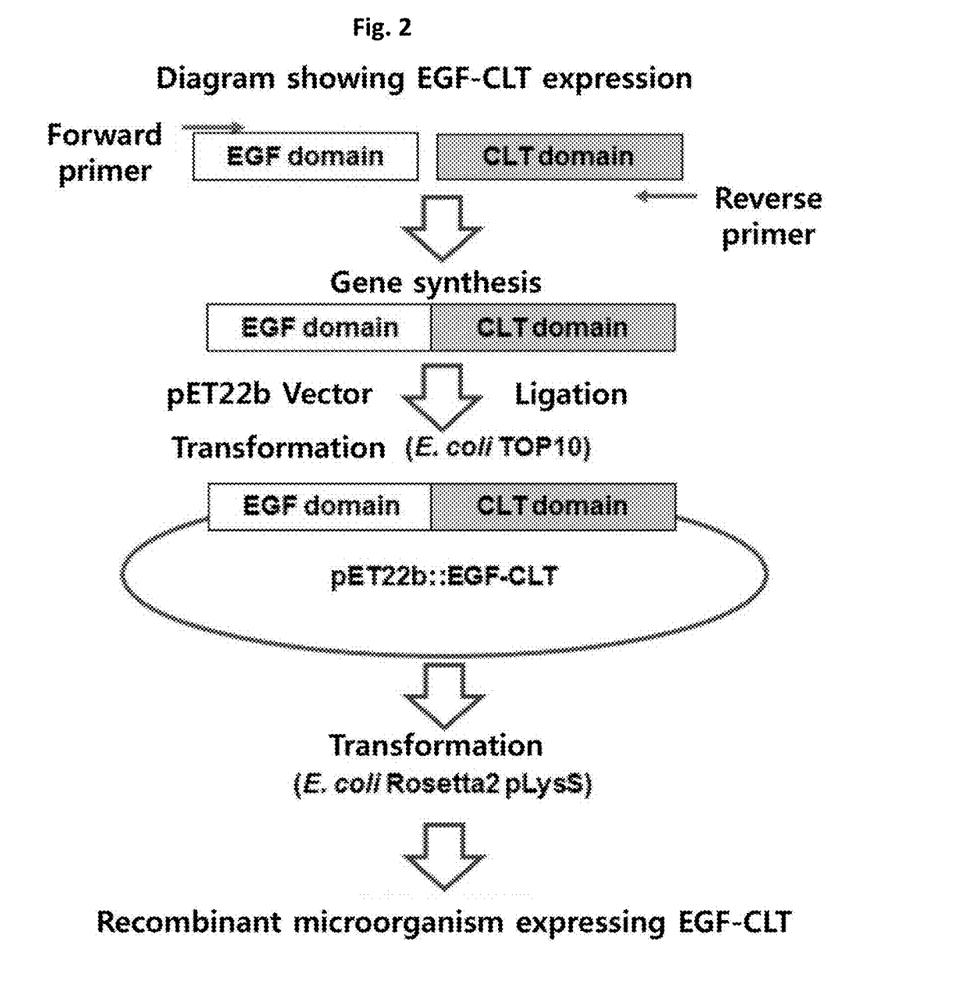
FIG. 2 is a schematic drawing illustrating the preparation of a recombinant plasmid (pET22b::EGF-CLT) of a fusion gene including human epidermal growth factor and scorpion toxin, and transformation with the recombinant plasmid.

The above gene fragment and recombinant plasmid were digested and inserted by using the same restriction enzymes (5' terminal NdeI restriction enzyme site (CATATG) and 3' terminal XhoI restriction enzyme site (CTCGAG)), and thus the recombinant plasmid shown in FIG. 1 (pET22b::EGF-CLT) and the recombinant plasmid shown in FIG. 2 (pET22b::EGF-CLT) were prepared. *E. coli* TOP10 was then transformed with each of the recombinant plasmid (pET22b::TRX-CLT, pET22b::EGF-CLT) product which has been prepared above so that a gene construct was obtained in large amount from the host microorganism.

*E. coli* Rosetta2 (DE3) pLysS (Novagen) was transformed with each of the recombinant plasmid (pET22b::TRX-CLT, pET22b::EGF-CLT) product which has been prepared above, and thus a recombinant microorganism for producing a fusion protein including the human thioredoxin and scorpion toxin or a fusion protein including the human epidermal growth factor and scorpion toxin, in which the gene construct is inserted to the host microorganism, was prepared. Diagrams with further details are given in FIG. 1 and FIG. 2.

Example 2. Expression Induction and Separation of Fusion Protein Including the Human Thioredoxin and Scorpion Toxin or Fusion Protein including the Human Epidermal Growth Factor and Scorpion Toxin E. coli Rosetta2 (DE3) pLysS (Novagen) prepared in Example 1 was cultured till to have $OD_{600}$=0.6 to 0.8 when it was batch-cultured using 1 L LB or BSB medium or $OD_{600}$=15 to 20 when it was continuously cultured using a 20 L fermenter. After that, it was added with 1 to 5 mM (final concentration) IPTG or 0.2 to 2% (final concentration) lactose to induce the expression of the genes in clone. After further culture for 4 hours to 5 hours, the cells were collected by centrifuge. The cells were completely suspended in a buffer solution (Phosphate buffered saline, NaCl 8 g, KCl 0.2 g, $Na_2HPO_4$ 1.44 g, $KH_2PO_4$ 0.24 g/L, pH 7.4), and the cells were disrupted by using a ultrasonic homogenizer. Accordingly, a solution containing intracellular proteins was separated.

Figure 3:
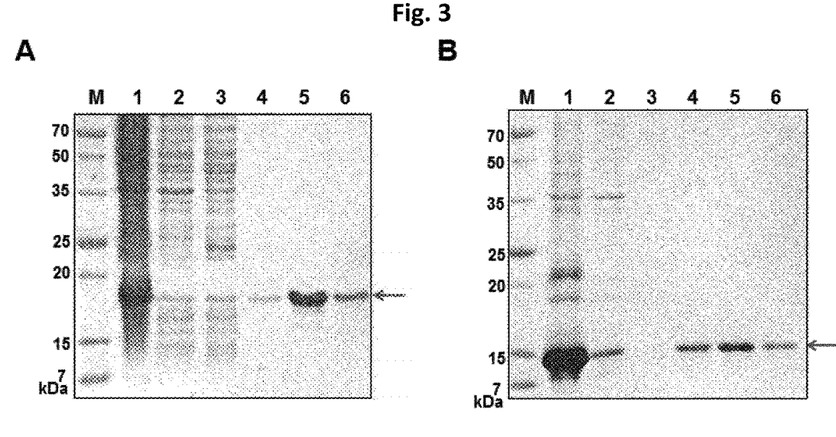
FIG. 3 shows the expression and purification of a fusion protein according to confirmation by 15% SDS-polyacrylamide gel electrophoresis. M represents DokDo-MARK (Broad range, un-stained, Elpis Biotech). A of FIG. 3 represents the expression and purification of a fusion protein including human thioredoxin and scorpion toxin (TRX-CLT), and B of FIG. 3 represents the expression and purification of a fusion protein including human epidermal growth factor and scorpion toxin (EGF-CLT).

From FIG. 3, it was able to confirm that the fusion protein including the human thioredoxin and scorpion toxin and fusion protein including the human epidermal growth factor and scorpion toxin are overexpressed.

Example 3. Measurement of Activity (Cell Proliferation Effect) of Fusion Protein Including the Human Thioredoxin and Scorpion Toxin or Fusion Protein Including the Human Epidermal Growth Factor and Scorpion Toxin After collecting a sample from a fraction from which the presence of a fusion protein including the human thioredoxin and scorpion toxin or a fusion protein including the human epidermal growth factor and scorpion toxin has been confirmed, in which the proteins have been separated and purified in Example 2, the cell proliferation effect for HDFa cell was determined.

In order to measure the activity of a fusion protein including the human thioredoxin and scorpion toxin or a fusion protein including the human epidermal growth factor and scorpion toxin, cultured HDFa cell was treated with each of a fusion protein including the human thioredoxin and scorpion toxin and a fusion protein including the human epidermal growth factor and scorpion toxin at a concentration of 0, 0.02 ppm, 0.2 ppm, 2 ppm, or 20 ppm, and then cultured for 3 days at 37° C. After that, the presence or absence of the cell proliferation effect was determined based on crystal violet staining method.

Figure 4:
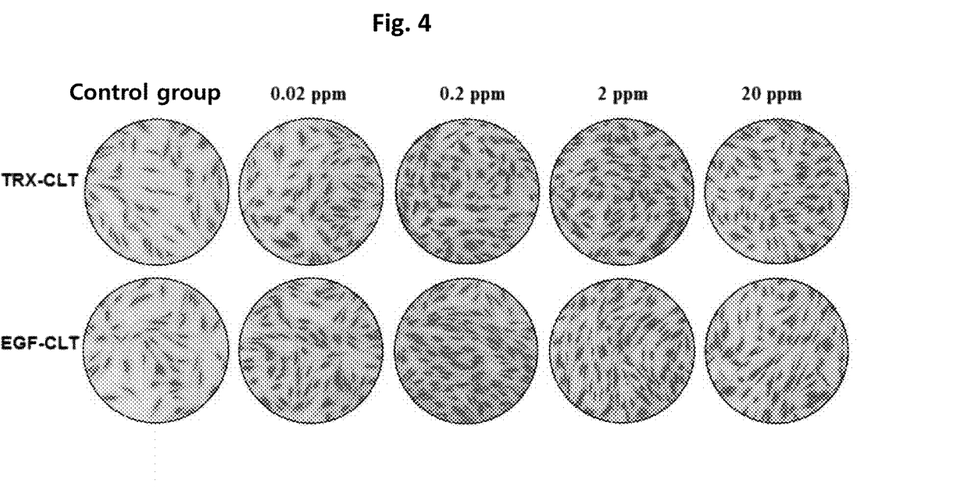
FIG. 4 is a photographic image for confirming the cell proliferation effect on human dermal fibroblasts adult (HDFa) cell, in which the image is obtained by treatment of HDFa cell with a fusion protein including human thioredoxin and scorpion toxin (TRX-CLT) or with a fusion protein including human epidermal growth factor and scorpion toxin (EGF-CLT) after isolation and purification of the fusion proteins.

As a result, it was found that the fusion protein including the human thioredoxin and scorpion toxin and the fusion protein including the human epidermal growth factor and scorpion toxin exhibit a cell proliferation effect for HDFa cell (FIG. 4).

Figure 5:
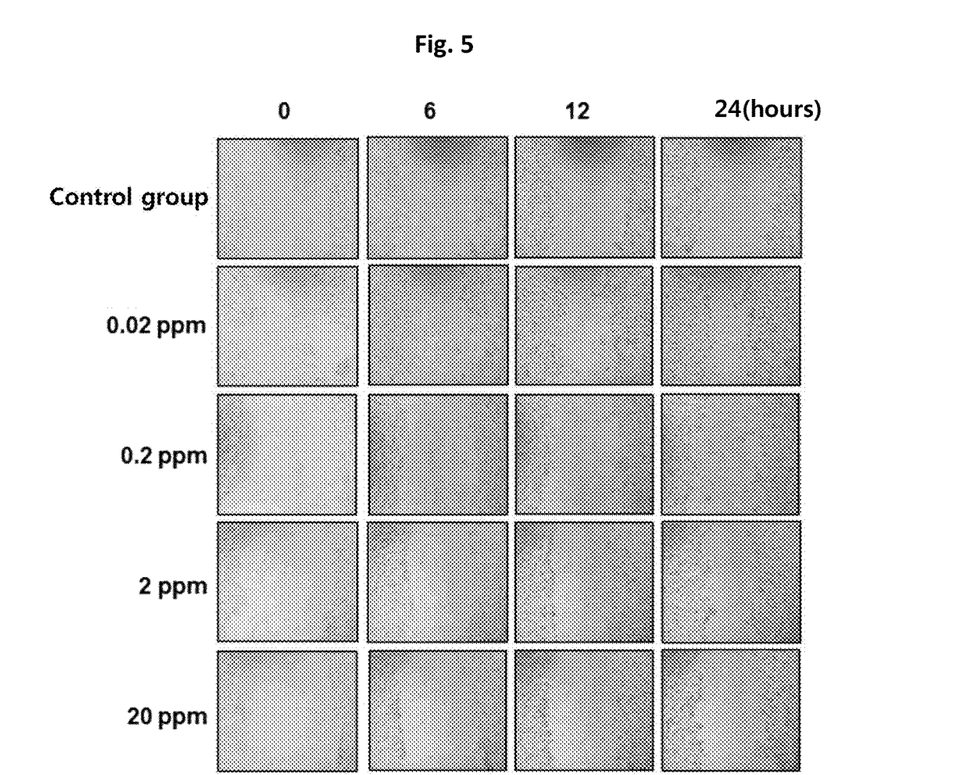
FIG. 5 is a photographic image obtained by observing, over 24 hours, the wound-healing effect for skin cell (HaCaT cell) by a fusion protein including human thioredoxin and scorpion toxin (TRX-CLT).
Figure 6:
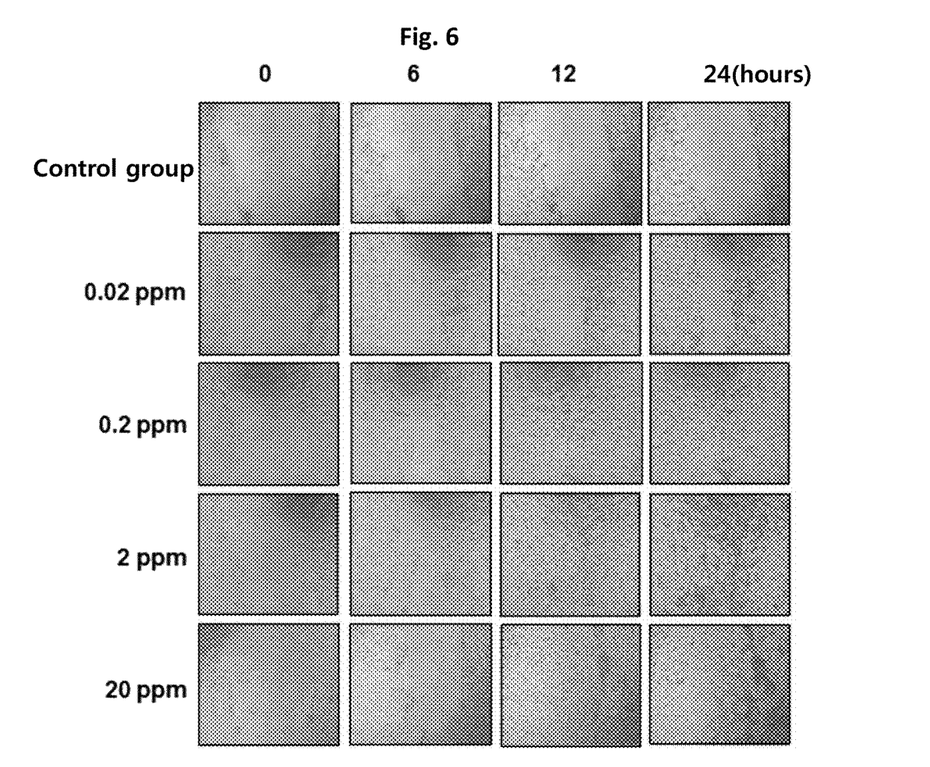
FIG. 6 is a photographic image obtained by observing, over 24 hours, the wound-healing effect for skin cell (HaCaT cell) by a fusion protein including human epidermal growth factor and scorpion toxin (EGF-CLT)

Example 4. Measurement of Activity (Cell Proliferation and Wound Healing in HaCaT Cell) of Fusion Protein Including the Human Thioredoxin and Scorpion Toxin or Fusion Protein Including the Human Epidermal Growth Factor and Scorpion Toxin After collecting a sample from which the presence of a fusion protein including the human thioredoxin and scorpion toxin or a fusion protein including the human epidermal growth factor and scorpion toxin has been confirmed, in which the proteins have been separated and purified in Example 2, the cell proliferation and wound healing in HaCaT cell (Human, Adult, low Calcium, High Temperature, epithelial keratinocyte) was determined. With regard to FIGS. 5 and 6, HaCaT cells were cultured and then treated with a fusion protein including the human thioredoxin and scorpion toxin or a fusion protein including the human epidermal growth factor and scorpion toxin, each at concentration of 0 to 20 ppm, and the wound healing effect on HaCaT cell was observed for 24 hours by using a microscope (Olympus CK40). When compared to the control group, the HaCaT cell treated with a fusion protein including the human thioredoxin and scorpion toxin or a fusion protein including the human epidermal growth factor and scorpion toxin, each at concentration of 0.02 to 20 ppm, exhibited a wound healing effect. From the results of FIGS. 5 and 6, it was recognized that the fusion protein including the human thioredoxin and scorpion toxin and the fusion protein including the human epidermal growth factor and scorpion toxin can exhibit the wound healing effect even at low concentration.

Figure 7:
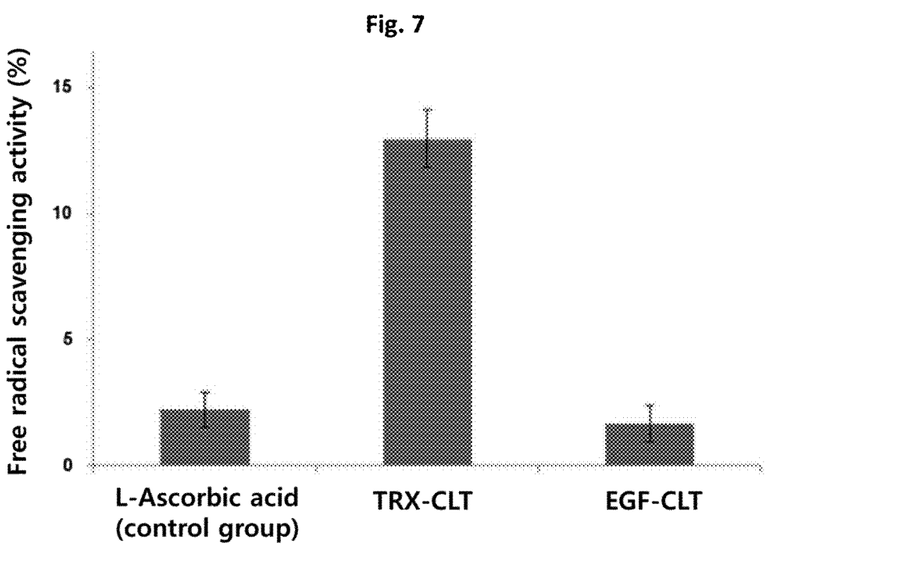
FIG. 7 shows a result of measuring free radical scavenging effect, in which the measurement has been carried out for determining the anti-oxidation effect of a fusion protein including human thioredoxin and scorpion toxin (TRX-CLT) and a fusion protein including human epidermal growth factor and scorpion toxin (EGF-CLT).

Example 5. Measurement of Activity (Anti-Oxidation Effect) of Fusion Protein Including the Human Thioredoxin and Scorpion Toxin or Fusion Protein Including the Human Epidermal Growth Factor and Scorpion Toxin FIG. 7 shows a result relating to the anti-oxidation effect of a fusion protein including human thioredoxin and scorpion toxin and a fusion protein including human epidermal growth factor and scorpion toxin. In order to measure the anti-oxidation effect of a fusion protein including human thioredoxin and scorpion toxin and a fusion protein including human epidermal growth factor and scorpion toxin, the DPPH method (1,1-diphenyl-2-pycryl-hydrazyl method), which is one of the methods for measuring the free radical scavenging effect, was used. This reagent is present as a relatively stable free radical, and the DPPH method is one of the in vitro methods that are primarily used in general to confirm the free radical scavenging effect.

In order to see the anti-oxidation effect of a fusion protein including human thioredoxin and scorpion toxin and a fusion protein including human epidermal growth factor and scorpion toxin, L-ascorbic acid was used as a control group. For the test, a fusion protein including human thioredoxin and scorpion toxin, a fusion protein including human epidermal growth factor and scorpion toxin, and L-ascorbic acid were prepared each at 1 µM concentration while DPPH was prepared at concentration of 0.2 mM. After mixing each of them at a ratio of 1:1, they were allowed to stand for 30 minutes at 37° C. After that, the absorbance was measured by using 520 nm ELISA reader. The free radical scavenging activity (%) was calculated based on the following equation 1, and the results are shown in FIG. 7.

$$\text{Free radical scavenging activity (\%)}=100-((B/A)*100) \quad \text{[Equation 1]}$$

A: Absorbance by control group which has not been treated with any test sample

B: Absorbance by test group which has been treated with test sample

Figure 8:
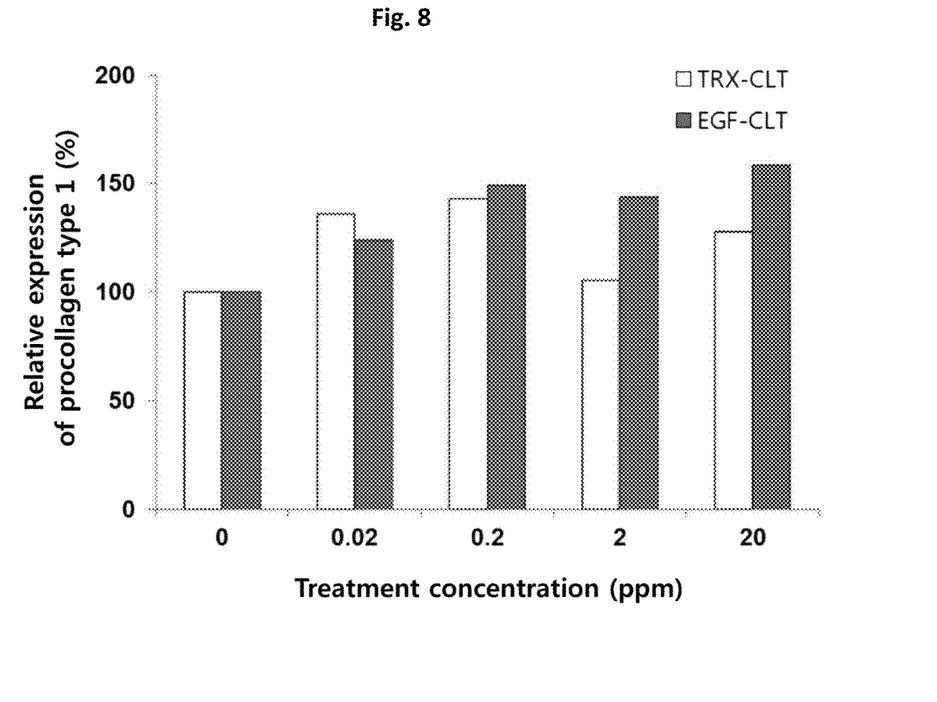
FIG. 8 shows a result of collagen synthesis by a fusion protein including human thioredoxin and scorpion toxin (TRX-CLT) and a fusion protein including human epidermal growth factor and scorpion toxin (EGF-CLT).

As a result, it was shown that the fusion protein including human thioredoxin and scorpion toxin showed the free radical scavenging activity that is about 4 times higher than that of the L-ascorbic acid control group while the fusion protein including human epidermal growth factor and scorpion toxin showed almost the same free radical scavenging activity as the L-ascorbic acid control group (FIG. 7). As such, it was found that an excellent skin anti-aging effect based on anti-oxidation activity is exhibited by the fusion protein including human thioredoxin and scorpion toxin and the fusion protein including human epidermal growth factor and scorpion toxin, in particular, by the fusion protein including human thioredoxin and scorpion toxin Example 6. Evaluation of Expression of Procollagen Type-1 in Fibroblast by Fusion Protein Including the Human Thioredoxin and Scorpion Toxin or Fusion Protein Including the Human Epidermal Growth Factor and Scorpion Toxin To see any promoted synthesis of collagen fiber that is one of the ways for suppressing skin aging caused by ultraviolet ray stimulation, fibroblast was treated with the proteins of the present invention and an evaluation was made in terms of promoted collagen synthesis. 72 Hours after treating fibroblast with a fusion protein including the human thioredoxin and scorpion toxin or with a fusion protein including the human epidermal growth factor and scorpion toxin at concentration of 0 to 20 ppm in serum free DMEM medium, a change in expression amount of procollagen type-1 was measured for cell extract as a subject by using Collagen-I ELISA kit (Cloud-Clone Corp., USA). The results are as shown in FIG. 8. As it can be confirmed from FIG. 8, the expression amount of procollagen type-1 increased in a manner that is dependent on concentration of the fusion protein including the human epidermal growth factor and scorpion toxin. On the other hand, in case of the fusion protein including the human thioredoxin and scorpion toxin, there was an increase in concentration dependent manner when the concentration is 0.2 ppm or lower. However, a decreasing pattern was observed above that concentration. This result was found to be coincident with the result showing the fibroblast proliferation effect as it is illustrated in FIG. 4. Accordingly, it was confirmed from FIG. 8 that skin aging, in particular, skin wrinkle caused by loss of collagen can be suppressed by the protein of the present invention.

The invention claimed is:

1. A fusion protein consists of the amino acid sequence of SEQ ID NO: 3 or SEQ ID NO: 4.

2. The fusion protein of claim 1, consisting of the amino acid sequence of SEQ ID NO: 4.

3. A gene encoding the fusion protein of claim 1.

4. The gene according to claim 3, wherein the gene consists of the *E. coli* (*Escherichia coli*) codon-optimized nucleotide sequence of SEQ ID NO: 1.

5. The gene according to claim 3, wherein the gene consists of the *E. coli* codon-optimized nucleotide sequence of SEQ ID NO: 2.

6. A recombinant vector comprising the gene of claim 3.

7. A host cell transformed with the recombinant vector of claim 6.

8. A method for producing a fusion protein in a host cell, the method comprising transforming a host cell with the recombinant vector of claim 6 to overexpress the fusion protein.

9. The method of claim 8, wherein the host cell is *E. coli*.

10. A cosmetic composition comprising the fusion protein of claim 1.

11. The fusion protein of claim 1, consisting of the amino acid sequence of SEQ ID NO: 3.

12. A recombinant vector comprising the gene of claim 4.

13. A recombinant vector comprising the gene of claim 5.

14. A method of enhancing skin cell proliferation and anti-oxidation activity of a subject, the method comprising:
applying the fusion protein of claim 1 to the subject.

15. The method of claim 14, wherein the fusion protein consists of the amino acid sequence of SEQ ID NO: 3.

16. The method of claim 14, wherein the fusion protein consists of the amino acid sequence of SEQ ID NO: 4.

17. A method of improving at least one of skin wrinkle, skin elasticity, and anti-aging, the method comprising:
applying a composition comprising the fusion protein of claim 1 to the subject.

18. The method of claim 17, wherein the fusion protein consists of the amino acid sequence of SEQ ID NO: 3.

19. The method of claim 17, wherein the fusion protein consists of the amino acid sequence of SEQ ID NO: 4.

* * * * *

SEQUENCE LISTING

<160> NUMBER OF SEQ ID NOS: 12

<210> SEQ ID NO 1
<211> LENGTH: 423
<212> TYPE: DNA
<213> ORGANISM: Artificial Sequence
<220> FEATURE:
<223> OTHER INFORMATION: TRX-CLT

<400> SEQUENCE: 1

```
atggtgaagc agatcgagag caagactgct tttcaggaag ccttggacgc tgcaggtgat      60
aaacttgtag tagttgactt ctcagccacg tggtgtgggc cttgcaaaat gatcaagcct     120
ttctttcatt ccctctctga aaagtattcc aacgtgatat tccttgaagt agatgtggat     180
gactgtcagg atgttgcttc agagtgtgaa gtcaaatgca tgccaacatt ccagtttttt     240
aagaagggac aaaaggtggg tgaatttct ggagccaata aggaaaagct tgaagccacc      300
attaatgaat tagtctgcat gccgtgcttc accaccgacc accagatggc gcgtaaatgc     360
gacgactgct gcggtggtaa aggtcgtggt aaatgctacg gtccgcagtg cctgtgccgt     420
tga                                                                   423
```

<210> SEQ ID NO 2
<211> LENGTH: 270
<212> TYPE: DNA
<213> ORGANISM: Artificial Sequence
<220> FEATURE:
<223> OTHER INFORMATION: EGF-CLT

<400> SEQUENCE: 2

```
atgaactcag actctgagtg cccactgtct cacgacggct actgccttca cgacggagtc      60
tgcatgtaca tcgaggcttt ggataagtac gcttgtaatt gcgtcgttgg ttacattgga     120
gagcgctgcc aataccgtga cttaaaatgg tgggagttgc gctgcatgcc gtgcttcacc     180
accgaccacc agatggcgcg taaatgcgac gactgctgcg gtggtaaagg tcgtggtaaa     240
tgctacggtc cgcagtgcct gtgccgttga                                      270
```

<210> SEQ ID NO 3
<211> LENGTH: 140

```
<212> TYPE: PRT
<213> ORGANISM: Artificial Sequence
<220> FEATURE:
<223> OTHER INFORMATION: TRX-CLT

<400> SEQUENCE: 3

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
                20                  25                  30

Gly Pro Cys Lys Met Ile Lys Pro Phe Phe His Ser Leu Ser Glu Lys
            35                  40                  45

Tyr Ser Asn Val Ile Phe Leu Glu Val Asp Val Asp Asp Cys Gln Asp
        50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val Cys Met Pro Cys Phe Thr Thr
            100                 105                 110

Asp His Gln Met Ala Arg Lys Cys Asp Asp Cys Cys Gly Gly Lys Gly
        115                 120                 125

Arg Gly Lys Cys Tyr Gly Pro Gln Cys Leu Cys Arg
    130                 135                 140

<210> SEQ ID NO 4
<211> LENGTH: 89
<212> TYPE: PRT
<213> ORGANISM: Artificial Sequence
<220> FEATURE:
<223> OTHER INFORMATION: EGF-CLT

<400> SEQUENCE: 4

Met Asn Ser Asp Ser Glu Cys Pro Leu Ser His Asp Gly Tyr Cys Leu
1               5                   10                  15

His Asp Gly Val Cys Met Tyr Ile Glu Ala Leu Asp Lys Tyr Ala Cys
                20                  25                  30

Asn Cys Val Val Gly Tyr Ile Gly Glu Arg Cys Gln Tyr Arg Asp Leu
            35                  40                  45

Lys Trp Trp Glu Leu Arg Cys Met Pro Cys Phe Thr Thr Asp His Gln
        50                  55                  60

Met Ala Arg Lys Cys Asp Asp Cys Cys Gly Gly Lys Gly Arg Gly Lys
65                  70                  75                  80

Cys Tyr Gly Pro Gln Cys Leu Cys Arg
                85

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
aaggagatat acatatggtg aagcagatcg ag                                    32

<210> SEQ ID NO 6
<211> LENGTH: 35
<212> TYPE: DNA
<213> ORGANISM: Artificial Sequence
```

<220> FEATURE:
<223> OTHER INFORMATION: primer

<400> SEQUENCE: 6
cgtcacggac acggcagact aattcattaa tggtg       35

<210> SEQ ID NO 7
<211> LENGTH: 37
<212> TYPE: DNA
<213> ORGANISM: Artificial Sequence
<220> FEATURE:
<223> OTHER INFORMATION: primer

<400> SEQUENCE: 7
caccattaat gaattagtca tgtgcatgcc gtgcttc     37

<210> SEQ ID NO 8
<211> LENGTH: 37
<212> TYPE: DNA
<213> ORGANISM: Artificial Sequence
<220> FEATURE:
<223> OTHER INFORMATION: primer

<400> SEQUENCE: 8
gaagcacggc atgcacatga ctaattcatt aatggtg     37

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
aaggagatat acatatgaac tcagactctg agtgc       35

<210> SEQ ID NO 10
<211> LENGTH: 34
<212> TYPE: DNA
<213> ORGANISM: Artificial Sequence
<220> FEATURE:
<223> OTHER INFORMATION: primer

<400> SEQUENCE: 10
ggtggtggtg ctcgagacgg cacaggcact gcgg        34

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
aaatggtggg agttgcgcat gtgcatgccg tgcttc      36

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
gaagcacggc atgcacatgc gcaactccca ccattt      36